United States Patent [19]

Pandey et al.

[11] Patent Number: 5,654,439
[45] Date of Patent: Aug. 5, 1997

[54] N-1-ALKYL-2,5-DI(TRIALKYL SILYL) PYRROLIDINES

[75] Inventors: Ganesh Pandey; Trusar Damu Bagul; Gingipalli Lakshmaiah, all of Maharashtra, India

[73] Assignee: Council of Scientific & Industrial Research, New Delhi, India

[21] Appl. No.: 574,349

[22] Filed: Dec. 18, 1995

Related U.S. Application Data

[62] Division of Ser. No. 490,862, Jun. 15, 1995, Pat. No. 5,510,490, which is a division of Ser. No. 179,304, Jan. 11, 1994, abandoned.
[51] Int. Cl.$^6$ ........................................................ C07F 7/02
[52] U.S. Cl. ............................................................. 548/406
[58] Field of Search ............................................. 548/406

[56] References Cited

PUBLICATIONS

Pandey, G. "Efficient Generation . . . " Tetrahedron Letters, vol. 34, No. 45, pp. 7301–7304, 1993.
Pandey, G. "An Expeditious Synthesis . . . " Tetrahedron Letters, vol. 35, No. 40, pp. 7439–7442, 1994.
Broka, C. "Total Synthesis . . . " CA 119(23) : 250211C (1993).
Corey, E.J. et al. "Stereo–controlled total," CA 120 (7); 77489 v 1993.

*Primary Examiner*—Amelia Owens
*Attorney, Agent, or Firm*—Ladas & Parry

[57] ABSTRACT

A novel 6-chloro-3-vinyl-pyridine of formula

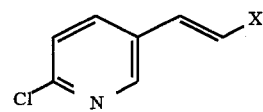

where X represents —H, —SO$_2$Ph, —CO$_2$Et, —COCH$_3$ and —CHO; which is used for the synthesis of Epibatidine of formula

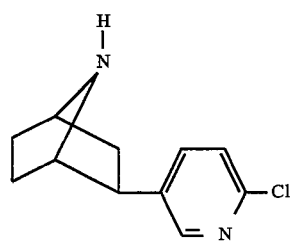

by reacting said 6-chloro-3-vinyl pyridine with N-1-alkyl-2,5-di(trialkyl silyl) pyrrolidine of formula

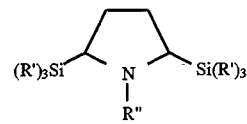

to obtain N-alkyl Epibatidine which is hydrogenated to obtain the Epibatidine.

11 Claims, 1 Drawing Sheet

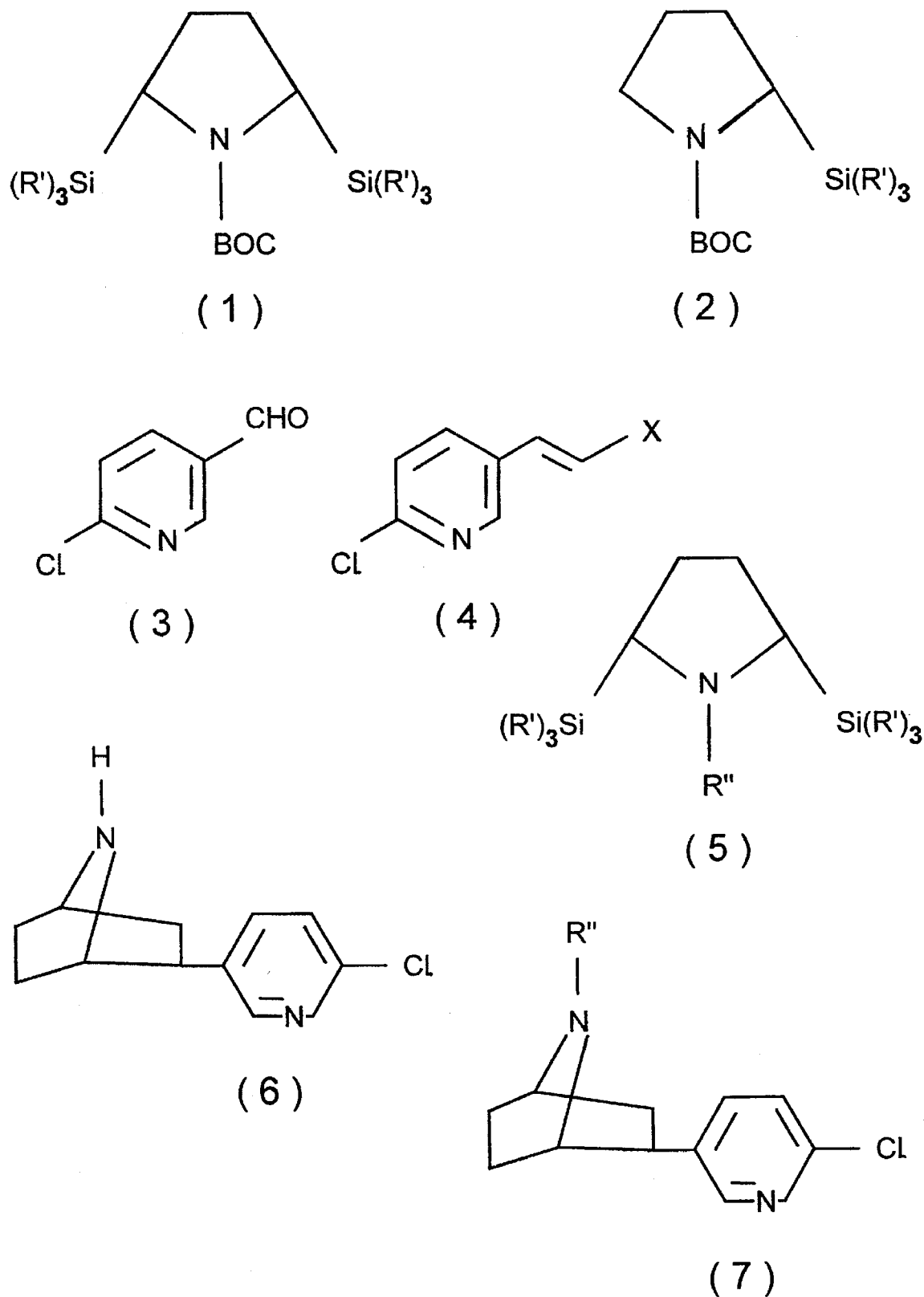
F I G. 1

N-1-ALKYL-2,5-DI(TRIALKYL SILYL) PYRROLIDINES

This is a divisional of application Ser. No. 08/490,862 filed Jun. 15, 1995 now U.S. Pat. No. 5,510,490 which is a divisional of Ser. No.: 08/179,304 filed Jan. 11, 1994 now abandoned.

FIELD OF THE INVENTION

This invention relates to a process for the synthesis of Epibatidine. The epibatidine prepared by the process of the present invention has the formula (6) shown in the drawing accompanying this specification. Epibatidine is a potent non-opiod analgesic.

BACKGROUND OF THE INVENTION

Epibatidine of the formula (6) hitherto was isolated from the skin of the Equadorian poison frog (Epibedobates tricolor). This alkaloid, present in trace amount, was isolated from the methanolic extracts of the frog's skin. Epibatidine so isolated exhibits strong analgesic activity (Thomas F. S.; Hugo M. G.; Micheal W. E; Heraman J. C. Y.; Lewis P and Daly J. W. J. Am. Chem. Soc. 1992 114, 3475–78). The potency of Epibatidine relative to morphine is about 200 times more. In addition, Epibatidine has a very low affinity for opiod receptors since it is nearly 9000-fold less potent than morphine at such receptors. Epibatidine possesses the 2-(chloro-pyridyl)-7-azabicyclo 2.2.1)-heptane skeleton a shown in the formula (6) and has been isolated from frog skin in very minute quantities (2 mg from 750 frog skins) employing the above mentioned procedure.

SUMMARY OF THE INVENTION

In view of immense biological activity associated with this molecule, we have developed an unprecedented approach for the preparation of Epibatidine.

BRIEF DESCRIPTION OF THE DRAWING

FIG. 1 shows formulas (1)–(7).

DETAILED DESCRIPTION OF THE INVENTION

The crux of the present invention relates to the synthesis of Epibatidine by reacting 6-chloro-3-vinyl pyridine of the formula (4) of the accompanying FIG. 1 where X represents $-CO_2Et$, $-CHO$, $-SO_2PH$, $-COCH_3$ and $-H$; with N-1-alkyl-2,5-di(trialkyl silyl) pyrrolidine of formula (5) of the accompanying FIG. 1, where R' represents any alkyl group such as methyl or ethyl and R" represents any alkyl group such as methyl, ethyl or benzyl.

BRIEF DESCRIPTION OF THE DRAWING

FIG. 1 shows the formulas of 2,5-di(trialkyl silyl) pyrrolidine t-butyl carbamate (1); 2-trialkyl silyl pyrrolidine t-butyl carbamate (2); 6-chloro-3 pyridine carboxyaldehyde (3); 6-chloro-3-vinyl pyridine (4); N-1-alkyl-2,5-di(trialkyl silyl) pyrrolidine (5); epibatidine (6) and N-alkyl epibatidine (7). The N-1-Alkyl-2,5-di(trialkyl silyl) Pyrrolidine is prepared by (a) treating a solution of 2-trialkyl silyl pyrrolidine t-butyl carbamate of formula (2) of the accompanying FIG. 1 where R' represents an alkyl group such as methyl or ethyl in an organic solvent with tetramethyl ethylene diamine and s-BuLi at a temperature at a range of –60° to –80° C., (b) adding chloro trialkyl silane to the reaction mixture;

(c) bringing the reaction temperature to room temperature, (d) quenching with 10% aqueous ammonium chloride solution;

(e) extracting the reaction mixture with an organic solvent;

(f) evaporating the solvent to give 2,5-di(trialkyl silyl) pyrrolidine t-butyl carbamate of the formula (1) of the accompanying FIG. 1 where R' represents any alkyl group such as methyl or ethyl; and thus obtained 2,5 di(trialkyl silyl) pyrrolidine t-butyl carbamate of formula (1) is subjected to the following steps namely, (g) deprotection of t-butyl carbamate group therein by an conventional method;

(f) refluxing the resulting deprotected free 2,5-di(trialkyl silyl) pyrrolidine in an organic solvent in the presence of an alkyl halide and inorganic base; and (i) filtering and evaporating the organic solvent to yield a novel N-1-alkyl 2,5-di(trialkyl silyl) pyrrolidine of the formula (5).

The organic solvent which is employed in step (a) and (e) may be selected from ether tetrahydro furan, di isopropyl ether and the like. The amount of tetramethyl ethylene diamine, s-BuLi and choloro trialkyl silane may range from 1 to 2 moles.

Examples 1 to 3 of the present specification typically illustrate the novel process for the preparation of 2,5-di (trialkyl silyl) pyrrolidine t-butyl carbamate.

The deprotection of t-butyl carbamate group in 2,5-di (trialkyl silyl) pyrrolidine t-butyl carbamate of the formula (1) may be carried out by treating it with trifluroacetic acid, p-toluene sulfonic acid or sodium hydroxide in polar organic solvent. The polar organic solvents used may be selected from dichloromethane, ether, benzene or dichloromethane ethyl acetate and the like. The solvent used for refluxion may be selected from acetonitrile, dimethyl formamide or ether. The inorganic base used may be selected from sodium carbonate, potassium carbonate and like. The above step of reflexion is effected at a temperature in the range of 80° to 150° C.

Examples 4, 5 and 6 of the present invention clearly illustrate the synthesis of new N-1-alkyl-2,5-di(trialkyl silyl pyrrolidine of the formula (5).

Another starting material for the preparation of epibatidine, namely 6-chloro-3-vinyl pridine of the formula (4) where X represents $-CO_2Et$, $-CHO$, $-SO_2Ph$, $-COCH_3$ and $-H$ is a novel compound itself which is prepared by adding 6-chloro-3 pyridine carboxyaldehyde of the formula (3) of the accompanying FIG. 1 to the corresponding phosphorous ylide generated in situ by conventional methods.

By way of example the generation of the ylide in situ is accomplished by adding n-BuLi to the triphenyl alkyl phosphonium bromide where the alkyl group can be $-CHCO_2Et$, $-CHSO_2Ph$, $-CHCHO$, $-CHCOCH_3$ or $-CH_2$ etc. in polar organic solvent at a temperature selected in the range of –70° to –80° C. Examples 7 to 10 of the present specification illustrate the preparation of novel 6-chloro-3-vinyl-pyridine of formula (4) of the FIG. 1.

Thus, the main object of the present invention is to synthesis Epibatidine of formula (6) by reacting N-1-alkyl-2,5-di (trialkyl silyl) pyrroidine of formula (5) with 6-chloro-3- vinyl pyridine of formula (4).

The further object of the invention relates to synthesis of N-1-alkyl-2,5-di(trialkyl silyl) pyrrolidine from 2,5-di (trialkyl silyl) pyrrolidine-t-butyl-carbamate of formula (1).

3

Yet another object of the invention relates to the novel 6-chloro-3-vinyl-pyridine of formula (4) where X represents —H-CO$_2$Et, —SO$_2$Ph, —CHO, —COCH$_3$ and its preparation by adding 6-chloro-3-pyridine carboxyaldehyde of formula (3) of the FIG. 1 to the corresponding phosphorous ylide generated in situ.

Accordingly, the present invention provides a process for the synthesis of Epibatidine of formula (6) which comprises reacting 6-chloro-3-vinyl pyridine of the formula (4) where X represents CO$_2$Et, —CHO, —SO$_2$Ph, —COCH$_3$ and —H with N-1-alkyl-2,5-di(trialkyl silyl) pyrrolidine of the formula (5) where R" represents methyl, ethyl, benzyl and the like and R' represents any alkyl group such as methyl or ethyl at a temperature ranging from 0° to 30° C. in the presence of an organic solvent to produce N-alkyl Epibatidine of the formula (7) of the accompanying FIG. 1 where R" has the meaning given above and converting said N-alkyl Epibatidine to Epibatidine of formula (6) by catalytic hydrogenation by conventional methods.

The organic solvent employed may be selected from polar solvents such as acetonitrile or dichloromethane. The catalyst used for hydrogenation may be palladium over carbon.

The invention is described in detail in the Examples 11 to 13 which are provided by way of illustration only and should not be construed to limit the scope of the invention.

EXAMPLE 1

Preparation of 2,5-di(trialkyl silyl) pyrrolidine t-butyl carbamate.

2-trimethyl silyl pyrrolidine t-butyl carbamate of the formula (2) where R' represents methyl (10 gms) in 200 ml ether at −20° to −34° C. is treated with TMEDA (12 ml) followed by 1M s-BuLi in hexane (40 ml). The reaction mixture is stirred for 3.5 hours and treated with chlorotrimethyl silane (12 ml). The reaction temperature showly brought to room temperature and diluted with water. The mixture extracted with ether and the ether is removed to give 2,5-di(trimethylsilyl) pyrrolidine t-butyl carbamate of the formula (1) where R' is methyl in 40% yield.

EXAMPLE 2

2-triethyl silyl pyrrolidine t-butyl carbamate of the formula (2) of the FIG. 1 where R' represents ethyl (10 gms) in 100 ml ether at −70° to −80° C. is treated with TMEDA (20 ml) followed by 1M s-BuLi in hexane (40 ml). The reaction mixture stirred for 3.5 hours at −70° to −80° C. and treated with chlorotrimethyl silane (14 ml). The reaction temperature slowly brought to room temperature and diluted with water. The mixture extracted with ether and the ether is removed to give 2,5-di-(triethyl silyl)pyrrolidine t-butyl carbamate of the formula (1) where R' is ethyl in 65% yield.

EXAMPLE 3

2-trimethyl silyl pyrrolidine t-butyl carbamate of the formula (2) of the FIG. 1 where R' represents ethyl (10 gms) in 200 of ether at −70°–80° C. is treated with TMEDA (20 ml) followed by 1M s-BuLi in hexone (40 ml). The reaction mixture stirred for 3.5 hours and treated with chlorotriethyl silane (16 ml). The reaction temperature slowly brought to room temperature and diluted with water. The mixture extracted with ether and the ether is removed to give 2-trimethyl silyl-5-triethyl silyl pyrrolidine t-butyl carbamate of the formula (1) where R' is ethyl in 45% yield.

EXAMPLE 4

Preparation of N-1-alkyl-2,5-di(trialkyl silyl) pyrrolidine.

Solution of 2,5-di(trimethyl silyl) pyrrolidine t-butyl carbamate (5 ml) of the formula (1) of the FIG. 1 where R' is methyl in 50 ml of dichloromethane at 0° C. was added with trifluoroacetic acid 10 ml slowly. The resultant reaction mixture was stirred for 2 to 3 hours at room temperature. The reaction mixture was made alkaline by adding concentrated aqueous sodium hydroxide. The dichloromethane layer was separated and aqueous layer repeatedly extracted with dichloromethane. Finally, the combine dichloromethane layers were evaporated to give 2,5-di(trialkyl silyl) pyrrolidine in 90% yield.

The 2,5-di(trimethyl silyl) pyrrolidine (2 gms) was refluxed acetonitrile with benzyl chloride (2 ml) in the presence of potassium carbonate at 80° to 100° C. for 24 hours to give N-1-benzyl-2,5-di(trialkyl silyl) pyrrolidine of the formula (5) where R' is methyl and R" is benzyl in 80% yield.

EXAMPLE 5

Solution of 2,5-di(trialkyl silyl) pyrrolidine t-butyl carbamate (5 ml) of the formula (1) of the FIG. 1 where R' is ethyl in 100 ml of dichloromethane at 25° C. was added trifluoroacetic acid(1) ml) slowly. The resultant reaction mixture was stirred for 2 to 3 hours at room temperature. The reaction mixture was made alkaline by adding concentrated aqueous sodium hydroxide. The dichloromethane layer was separated and aqueous layer repeatedly extracted with dichloromethane. The combine dichloromethane layers were evaporated to give free amine in 70% yield.

The 2,5-di(trialkyl silyl) pyrrolidine (1.5 ml) was refluxed in acetonitrile with ethyl iodide (2 ml) in the presence of sodium carbonate at 80°–100° C. for 24 hours to give N-1-ethyl-2,5-di(triethyl silyl) pyrrolidine of the formula (5) where R' and R" are ethyl in 60% yield.

EXAMPLE 6

To a solution of 2,5-di(trialkyl silyl) pyrrolidine t-butyl carbamate of the formula (1) of the FIG. 1 where R' is methyl at room temperature was added p-toluene sulfonic acid. The resultant reaction mixture was stirred at 25° C. for 8 hours. The resultant reaction mixture was washed with concentrated aqueous sodium hydroxide and water. The ethyl acetate layer dried and give free amine in 70% yield.

The 2,5-di(trimethyl silyl) pyrrolidine (2 ml) is refluxed with benzyl chloride (1.9 ml) in acetonitrile in the presence of sodium carbonate to give N-1-methyl-2,5-di(trialkyl silyl) pyrrolidine or the formula (5) where R' is methyl and R" is benzyl in 80% yield.

EXAMPLE 7

Preparation of 6-chloro-3-vinyl pyridine of formula (4).

To the previously dried triphenyl methyl phosphonium iodide (1 mole) in tetrahydro furan at −70° C. the n-butyl lithium (1.1 mole was added dropwise to form the yield. The reaction mixture was stirred for 1 hour at −78° C. The 6-chloro-3 pyridine carboxyaldehyde of the formula (3) of the FIG. 1 in dry tetrahydrio furan was introduced to the reaction mixture. After stirring for 1 hour at −78° C. the temperature of the reaction mixture was slowly raised to 0° C. Thereafter, the reaction mixture was quenched with 10% ammonium chloride solution. The aqueous layer extracted with ether, the ether solvent was removed and the residue column chromatographed to give 6-chloro 3-vinyl pyridine of formula (5) where represents H in 70% yield.

EXAMPLE 8

To the previously dried triphenyl methyl phosphonium iodide (1 mole) in tetrahydro furan at −78° C., n-butyl lithium (1.1 mole) was added dropwise to form the ylide. The reaction mixture was stirred for 1 hour at −78° C. The 6-chloro-3 pyridine carboxyaldehyde of the formula (3) of the FIG. 1 in dry tetrahydrio furan was introduced to the reaction mixture. After stirring for 1 hour at −40° C. the temperature of the reaction mixture was slowly raised to 0° C. Thereafter, the reaction mixture was quenched with 10% ammonium chloride solution. The aqueous layer extracted with ether. The ether solvent was removed and the residue column chromatographed to give 6-chloro-3-vinyl pyridine of formula (4) where X represents H in 40% yield.

EXAMPLE 9

To the previously dried triphenyl methyl phosphonium bromide in tetrahydro furan at −78° C., in which the n-butyl lithium (1.1 mole) was added dropwise to form the ylide. The reaction mixture was stirred for 1 hour at −78° C. The 6-chloro-3 pyridine carboxyaldehyde of the formula (2) of the FIG. 1 in dry tetrahydric furan was introduced to the reaction mixture. After stirring for 1 hour, the reaction mixture temperature was slowly raised to 0° C. Reaction was quenched with 10% ammonium chloride solution. The aqueous layer extracted with ether. The ether solvent was removed and the residue column chromatographed to give 6-chloro-3-vinyl pyridine of formula (4) where X represents H in 30% yield.

EXAMPLE 10

To a solution of diethyl phenyl sulfono methyl phosphonate (10 gms) in ether at −78° C. was added 1M n-BuLi (22 ml) and the reaction mixture stirred for 3 hours at −78° C. The 6-chloro-3-vinyl pyridine carboxyaldehyde (5 gms) was introduced to the reaction mixture, the temperature was allowed to come to room temperature and stirred for 12 hours. The reaction was quenched with 10% ammonium chloride solution. The aqueous layer extracted with ether. The solvent removed and the residue being columned chromatographed to give 6-chloro-3-vinyl pyridine of the formula (4) where X represents —SO$_2$Ph (sulfono phenyl).

EXAMPLE 11

Synthesis of Epibatidine of the formula (6) of the FIG. 1

To a acetonitrile solution containing 3 gms of Ag (1) F. 1.2 gms of dipolrophile (6-chloro-3-vinyl pyridine) was added with 2 gms N-benzyl-2,5-di(trimethyl silyl) pyrrolidine at 15° C. After stirring the reaction mixture for 2 to 2.5 hours, the reactor mixture was filtered through a plug of celite. The solvent was evaporated to give N-benzyl Epibatidine in 50% yield, which was further purified by column chromatography. Hydrogenation of n-alkyl Epibatidine with pd/c for 22 hours gave Epibatidine in 70% yield.

EXAMPLE 12

To a dichloromethane solution containing 3 gms of Ag (1)F. 1.2 gms of dipolrophile (6-chloro-3-vinyl pyridine) was added to 2 gms of N-ethyl-2,5-di(triethyl silyl), pyrrolidine at 15° C. After stirring the reaction mixture for 2 to 2.5 hours the reaction mixture was filtered through a plug of celite. The solvent was evaporated to give n-ethyl Epibatidine in 40% yield which was further purified by column chromatography. Hydrogenation of N-ethyl Epibatidine with pd/c for 22 hours gave Epibatidine in 60% yield.

EXAMPLE 13

To a acetonitrile solution containing 3 gms of Ag (1)F. 1.2 gms of dipolarophile (6-chloro-3-vinyl pyridine) was added to 2 gms of N-methyl-2,5-di(trimethyl silyl) pyrrolidine at 25° C. After stirring the reaction mixture for 2 to 2.5 hours, the reaction mixture was filtered through a plug of celite. The solvent was evaporated to give N-methyl Epibatidine in 80% yield which was further purified by column chromatography. Hydrogenation of N-methyl Epibatidine with pd/c for 22 hours gave 70% yield of Epibatidine.

We claim:

1. N-1-alkyl-2,5-di (trialkyl silyl) pyrrolidine of formula

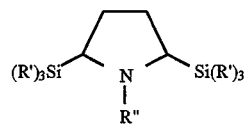

(5)

wherein R' and R" are both alkyl.

2. The N-1-alkyl-2,5-di(trialkyl silyl) pyrrolidine of claim 1 wherein R' is methyl or ethyl and R" is methyl, ethyl or benzyl.

3. A process for the synthesis of N-1-alkyl-2,5 di(trialkyl silyl) pyrrolidine of claim 1 of formula

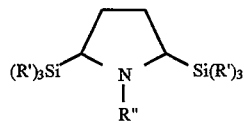

(5)

which comprises a) deprotecting the t-butyl carbamate group of 2,5 di(trialkyl silyl) pyrrolidine t-butyl carbamate of formula

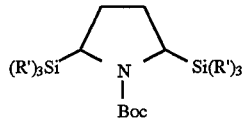

(1)

where R' represents an alkyl group;

(b) refluxing the deprotected 2,5 di(trialkyl silyl) pyrrolidine in an organic solvent in the presence of an alkyl halide and an organic base, and (c) filtering and evaporating the organic solvent to obtain N-1-alkyl-2,5 di(trialkyl silyl) pyrrolidine.

4. The process according to claim 3 wherein R' is methyl or ethyl and R" is methyl, ethyl or benzyl.

5. The process according to claim 3 wherein the deprotected 2,5 di(trialkyl silyl) pyrrolidine is refluxed at a temperature of from 80° to 150° C.

6. The process according to claim 3, wherein an organic solvent is used in step (a) and said organic solvent is selected from ethyl acetate, benzene, dichloromethane or ether.

7. The process according to claim 3, wherein the organic solvent used in step (b) is selected from acetonitrile, dimethyl formamide or ether.

8. 2,5 di(trialkyl silyl) pyrrolidine t-butyl carbamate of formula

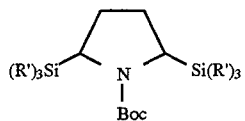

(1)

wherein R' represents alkyl.

9. The 2,5 di(trialkyl silyl) pyrrolidine t-butyl carbamate of claim 8 wherein R' is methyl or ethyl.

10. A process for the synthesis of 2,5-di(trialkyl silyl) pyrrolidine t-butyl carbamate of claim 8 of formula

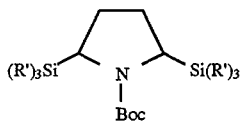

(1)

which comprises:

(a) treating a solution of 2-trialkyl silyl pyrrolidine t-butylcarbamate of formula

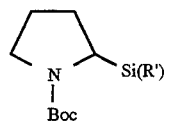

(2)

wherein $R^1$ is alkyl, in an organic solvent with tetra methyl ethylene diamine and N-butyllithium at −60° to −80° C., (b) adding chloro trialkyl silane to the reaction mixture, (c) bringing the mixture of step (b) to room temperature, (d) quenching the reaction mixture with ammonium chloride, (e) extracting with an organic solvent and (f) evaporating the solvent to give 2,5-di(trialkyl silyl) pyrrolidine t-butyl carbamate.

11. The process according to claim 10 where R' is methyl or ethyl.

* * * * *